US010413779B2

(12) United States Patent
Ingram et al.

(10) Patent No.: US 10,413,779 B2
(45) Date of Patent: Sep. 17, 2019

(54) TASK MODULATION FOR WELLNESS PROGRAMS

(71) Applicant: Welltok, Inc., Denver, CO (US)

(72) Inventors: Paul Ingram, Poulsbo, WA (US); Elizabeth Quinn, Seattle, WA (US); Travis McElfresh, Redmond, WA (US)

(73) Assignee: Welltok, Inc., Denver, CO (US)

( * ) Notice: Subject to any disclaimer, the term of this patent is extended or adjusted under 35 U.S.C. 154(b) by 120 days.

(21) Appl. No.: 15/186,169

(22) Filed: Jun. 17, 2016

(65) Prior Publication Data

US 2017/0365186 A1 Dec. 21, 2017

(51) Int. Cl.
| | |
|---|---|
| *A63B 24/00* | (2006.01) |
| *G09B 19/00* | (2006.01) |
| *H04W 4/02* | (2018.01) |
| *G09B 5/12* | (2006.01) |
| *G09B 7/04* | (2006.01) |
| *A61B 5/00* | (2006.01) |
| *G06Q 10/10* | (2012.01) |
| *A61B 5/11* | (2006.01) |
| *A63B 71/06* | (2006.01) |
| *G06Q 10/06* | (2012.01) |

(52) U.S. Cl.
CPC ........ *A63B 24/0062* (2013.01); *A61B 5/0022* (2013.01); *A61B 5/1118* (2013.01); *A63B 24/0059* (2013.01); *A63B 71/0622* (2013.01); *G06Q 10/0639* (2013.01); *G06Q 10/109* (2013.01); *G06Q 10/1097* (2013.01); *G09B 5/125* (2013.01); *G09B 7/04* (2013.01); *G09B 19/00* (2013.01); *G09B 19/003* (2013.01); *H04W 4/02* (2013.01); *A63B 2024/0065* (2013.01); *A63B 2024/0068* (2013.01)

(58) Field of Classification Search
None
See application file for complete search history.

(56) References Cited

U.S. PATENT DOCUMENTS

| | | | |
|---|---|---|---|
| 2007/0100595 | A1 | 5/2007 | Earles et al. |
| 2012/0116550 | A1 | 5/2012 | Hoffman et al. |
| 2012/0239451 | A1* | 9/2012 | Caligor .................. G06Q 10/00 705/7.21 |
| 2013/0216989 | A1 | 8/2013 | Cuthbert |
| 2015/0038806 | A1* | 2/2015 | Kaleal, III ........... A61B 5/4872 600/301 |
| 2015/0127265 | A1* | 5/2015 | Iizuka ................. G06F 19/3481 702/19 |
| 2015/0199010 | A1* | 7/2015 | Coleman .............. A61B 5/0006 345/156 |

(Continued)

*Primary Examiner* — Jason T Yen
(74) *Attorney, Agent, or Firm* — Perkins Coie LLP

(57) ABSTRACT

A system to assist users with the completion of tasks in a wellness program itinerary. The system assists users in completing tasks by recommending a controlled number of tasks for a user to perform in a next task period. The system determines the number of tasks to recommend by computing a pace that would enable the user to complete all wellness programs in the itinerary within a recommended time period. The system determines which tasks to recommend to the user based on several factors, such as a user state and user environment. The user environment is based on the location of the user, and may include the weather and surrounding landmarks at the location.

20 Claims, 14 Drawing Sheets

(56) References Cited

U.S. PATENT DOCUMENTS

2016/0196759 A1* 7/2016 Kim .................. G09B 5/02
                                                          434/247
2016/0220867 A1* 8/2016 Flaherty .............. G06F 19/3481
2016/0263439 A1* 9/2016 Ackland ............. G06F 19/3481
2017/0156666 A1* 6/2017 Surbur .................. A61B 5/681

* cited by examiner

| Wellness Program Identification Number | Wellness Program Name | Description | Length | Keywords | Tasks |
|---|---|---|---|---|---|
| 1435 | Introduction to Stress Reduction | A beginning wellness program that introduces the user to various relaxation strategies | 5 tasks to complete in 1 week | Stress, meditation, relaxation | 1 -- Video intro (5 min)<br>2 -- Stretching video (2 min) daily<br>3 -- Breathing exercises text<br>4 -- Journaling instruction<br>5 -- Quiz |
| 1440 | Introduction to Physical Fitness | A beginning wellness program that introduces the user to various physical exercises | 3 tasks to complete in 3 days | Exercise, work out, calisthenics | 1 -- Video intro (3 min)<br>2 -- Walk or run 10-15 min daily<br>3 -- Watch lecture on various workout classes (20 min) |
| 1450 | Introduction to Healthy Eating Habits | An introductory wellness program that introduces the user to various healthy foods | 4 tasks to complete in 3 weeks | Food, healthy diet, reduce weight | 1 -- Eat a piece of fruit twice per day<br>2 -- Drink 1 glass of water at meal per day<br>3 -- Substitute a whole-wheat product for a white-flour product<br>4 -- Watch an instructional video on healthy eating habits |
| 1452 | Advanced Healthy Eating Habits | A wellness program that builds on the introductory course and encourages healthy eating habits | 10 tasks to complete in 5 weeks | Food, healthy diet, reduce weight | 1 -- Keep a food journal of calorie consumption<br>2 -- Drink 1 glass of water at meal per day<br>3 -- Substitute a whole-grain product for a white-flour product<br>4 -- Watch an instructional video on healthy eating habits<br>5-10 -- Take a biometric exam in 5 areas |

*FIG. 3A*

| Task Number | Short Task Description | Estimated Task Length | Physical Activities | Weather Restrictions | Location Restrictions |
|---|---|---|---|---|---|
| 1 | Watch video clip | 15 min | Visual Acuity | None | None |
| 2 | Take survey | 5 min | None | None | None |
| 3 | Run 1 mile | 30 min | Run | Temperature greater than 35°F | None |
| 4 | Drink cup of water | 3 min | None | None | None |
| 5 | Lift weights | 30 min | Lift objects over 15 pounds | None | Gym within 10 miles |
| 6 | Walk in park | 20 min | Walk | No precipitation | Park within 5 miles |

*FIG. 3B*

| Physical Activity | Health Conditions that Prevent Physical Activity |
|---|---|
| Run | Leg pain<br>Influenza<br>Broken or sprained ankles<br>Knee injuries<br>... |
| Visual Acuity | Glaucoma<br>Retinal detachment<br>Cataracts |
| Lift objects more than 15 pounds | Neck pain<br>Back pain<br>Surgery within last 2-3 weeks<br>... |
| Walk | Leg pain<br>Neck pain<br>Back pain<br>... |

Home

Programs
My Programs
More Activities

Coaching
My Coaching Sessions
Video Coaching
Coaches

Resources
Blogs
Health Resources

Communities
Communities
Private Health Groups

Search

User #1  Sign Out

Healthy Habits -- Drink to Your Health

Wake Up, Drink Up!

Water is our body's principal chemical component, making up nearly 60 percent of our body weight. Every system in our bodies depends on water to function properly, and even mild dehydration can drain your energy and make you tired. Some researchers have even found that staying well hydrated can also boost metabolism and help with weight loss.

This week's healthy habit is Drink a glass of water every morning when you wake up.

I drank  1  glass of water.

on May 2, 2016

Log Now — 855

Health Habits -- Drink to Your Health

Build healthy habits one day at a time. This program focuses on the all-important habit of getting adequate hydration. Practice the suggested activities each week and build the foundation of a healthy lifestyle.

TASK MODULATION FOR WELLNESS PROGRAMS

BACKGROUND

A wellness program is a program typically offered by an employer, healthcare provider, or insurance company that is intended to improve and promote the health of employees and individuals. Wellness programs often include tasks for individuals to perform, such as participating in sponsored exercise, joining weight-loss competitions, attending diabetes management lectures, listening to educational seminars, and reading tobacco cessation literature. Wellness program tasks may also include screenings that are designed to monitor the physical health of individuals, such as measurement of blood pressure or glucose levels.

An employer, healthcare provider, insurance company, or other party controlling access to wellness programs (collectively, "sponsors") can offer a wellness program or a suite of wellness programs to a user such as an employee or an insured party. Wellness programs are often administered via a service platform such as a website or an application program. For example, a user can use a mobile application to access and participate in wellness programs. In such an example, a user can download the mobile application, register using a screen name linked to an email address, and select certain wellness programs in which to participate. Alternatively, a user can use a desktop or laptop computer to access a website and register for a service that provides wellness programs. The service can provide a set of wellness programs to a user, allowing the user to select desired programs in which to participate. For example, a working father may have a few fitness goals such as reducing stress, losing weight, and managing diabetes. He can access a website provided by a business that offers wellness programs to accomplish his goals.

Wellness programs can take a variety of forms, but typically are associated with one or more goals. Each goal is defined by one or more tasks to be completed by the user within a certain time period. Tasks are recommended activities for users to complete in furtherance of the goals of a wellness program. For example, the goal of a wellness program may be to reduce stress. The tasks in the wellness program may be to take a five-minute walk outside during the workday, to watch a short instructional video on stress reduction, or to journal thoughts at the end of each day. As another example, the goal of a wellness program may be to lower blood pressure. The tasks can include regularly (e.g., 15 minutes/day, every day) performing a cardiovascular exercise such as running or cycling over a one-month period.

Unfortunately, people struggle to effectively use wellness programs. One reason why people struggle to effectively use wellness programs is because they are overwhelmed with the number of tasks that need to be completed. Wellness programs often include several tasks (e.g., 5 or more) to be completed, and users typically participate in multiple, concurrent wellness programs (e.g., 3 or more). As a result, users have a large quantity of tasks to complete (e.g., 15 or more) in a given timeframe, which overwhelms the user and, in some cases, results in reduced motivation and desire to participate in a wellness program.

Another reason why people struggle to effectively use wellness programs is because the tasks associated with a wellness program may not be suitable for a user. One variable for determining if a task is suitable for a user is the surrounding physical facilities that either help or hinder the user in completing the task. For example, a user may have a task to run outside in a park, but a user may be located in an area that does not have a park in close proximity. The weather at the location of the user may also help or hinder the user. For example, a user may have a task to swim in a lake or an ocean, but the weather where the user is located may present cold and windy conditions that would make such swimming unpleasant or difficult. If conditions are not suitable for the user to complete the task, most users forgo the task and fail to make progress in completing wellness programs.

The need exists for systems and methods that overcome the above problems, as well as provide additional benefits. Other limitations of existing or prior systems will become apparent to those of ordinary skill in the art upon reading the following Detailed Description.

BRIEF DESCRIPTION OF THE DRAWINGS

FIG. 3A is a table with representative wellness program data.

FIG. 3B is a table with representative task data associated with a wellness program.

FIG. 3C is a table with representative data for physical activities and limiting health conditions.

FIGS. 7A-7B and 8A-8B are example graphical interfaces for the disclosed system.

Figure 1:
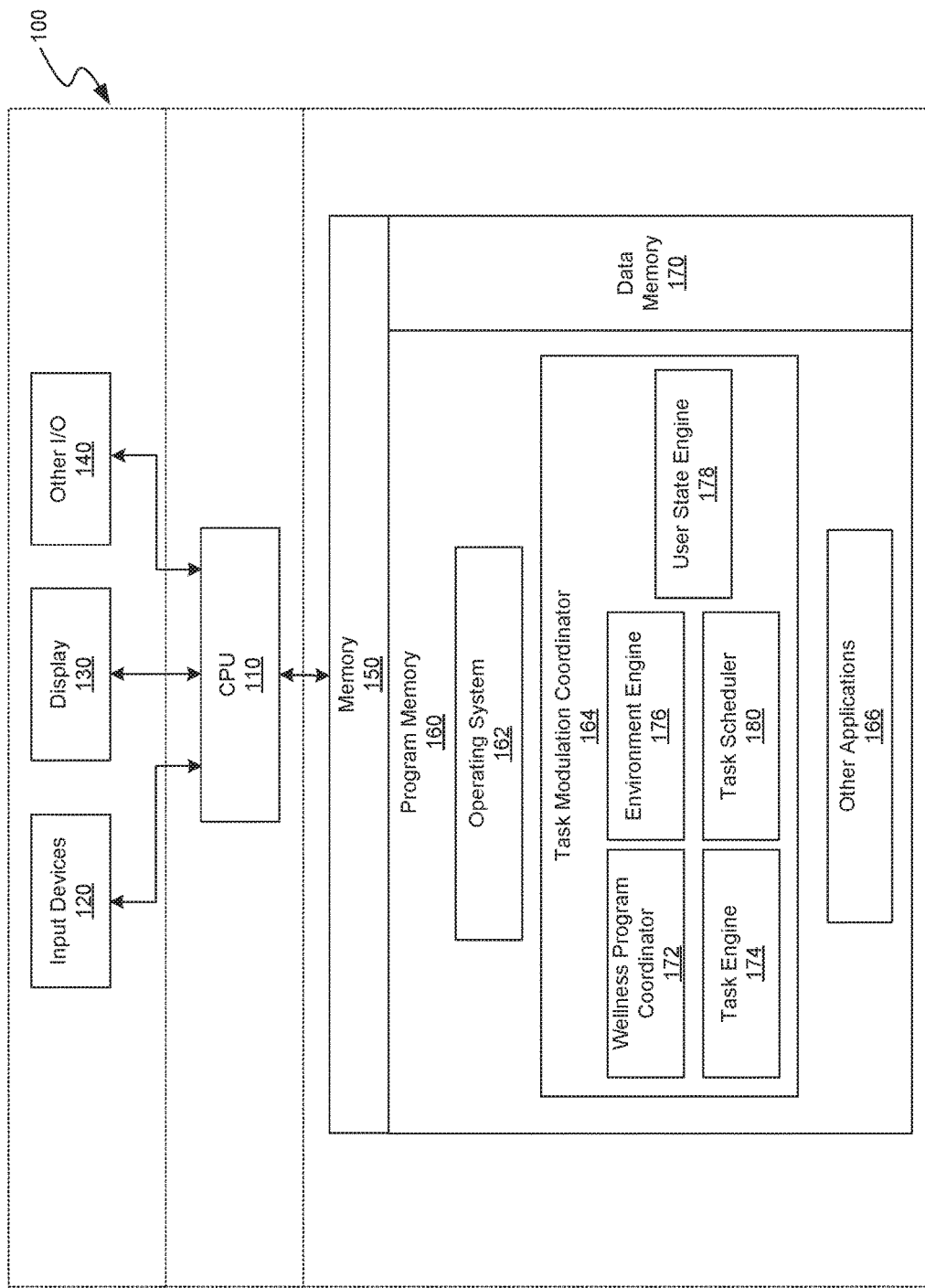
FIG. 1 is a block diagram illustrating a representative device on which the disclosed system for providing a modulated set of tasks associated with a wellness program itinerary operates.

The techniques introduced in this disclosure can be better understood by referring to the following Detailed Description in conjunction with the accompanying drawings.

DETAILED DESCRIPTION

A system to assist users in accomplishing health and fitness goals is disclosed herein. To assist a user in accomplishing health and fitness goals, the system allows the user to select or enroll in one or more wellness programs. A wellness program includes information related to health and fitness goals, a set of activities (also referred to as "tasks") to help the user accomplish those goals, and a recommended duration for completion of the wellness program (e.g., 10 weeks). From a set of wellness programs offered by the system, a user elects to participate in a subset of wellness programs. The selected set of wellness programs in which a user is enrolled or is participating is also referred to herein as an "itinerary." Because each wellness program can include multiple tasks, the sum total of tasks in a user's itinerary can be a large number. In order to avoid overwhelming the user with a large number of tasks to complete, the system recommends a subset of the total number of tasks to the user. The number of recommended tasks is based, in part, on the remaining length of time for completing the wellness programs in the itinerary. For example, in an itinerary that includes 10 wellness programs, each with an expected completion time of five weeks, and each with five tasks for a total of 50 tasks, the system can recommend two tasks per day to keep the user on track to finish the itinerary in five weeks. The average number of recommended tasks to complete all tasks in the user's itinerary within a recommended timeframe is referred to herein as the "task pace."

When recommending tasks to the user, the system may modify the type of task that is recommended to the user based on several factors. One factor used in modifying the recommended tasks is the characteristics of the environment in which the user is located. The environment of the user may include the surrounding physical location of the user as well as the weather at the location. Another factor used in modifying the recommended tasks is the physical state of the user. For example, if the user is injured or physically unable to complete a task, the system will not recommend the task to the user. Using one or more factors, the system updates the recommended tasks to the user.

In a representative use of the system, the system identifies tasks associated with a wellness program itinerary for a user, determines a recommended number of tasks to be completed in the next task period, receives user state and environment information, selects a set of recommended tasks from the tasks remaining in the itinerary to provide to the user based on the number of tasks, user state, and environment information, and provides the recommended tasks to a user. Once the tasks are presented to the user, the system tracks the user's progress in completing tasks based on feedback received from one or more mobile or wearable devices associated with the user or directly from the user. After a triggering event such as the end of a task period or an addition of a new wellness program to the user's itinerary, the system updates the recommended tasks based on the completed tasks, changes in environment, and changes in user state, and presents the updated recommended tasks to the user. The recommended tasks may include an increased, decreased, or same number of tasks as was presented for the previous task period. Moreover, the recommended tasks may include different tasks than the previous task period depending on the user's state, user's environment, and prior task completion.

There are several expected advantages to the disclosed system. First, the system can improve the motivation and focus of wellness program participants. By controlling the number of tasks presented to a user, the system prevents the user from being overwhelmed with tasks or losing motivation to complete tasks. Second, the system customizes a user's experience by matching recommended tasks with a user's current state and environment. By modulating the number and type of task presented to a user, the user may be more inclined to complete the presented tasks. Other advantages will be apparent to those having ordinary skill in the art when reading this Detailed Description.

Various implementations of the system will now be described. The following description provides specific details and an enabling description of these implementations. One skilled in the art will understand, however, that the system may be practiced without many of these details. Additionally, some well-known structures or functions may not be shown or described in detail so as to avoid unnecessarily obscuring the relevant description of the various implementations. The terminology used in the description presented below is intended to be interpreted in its broadest reasonable manner, even though it is being used in conjunction with a detailed description of certain specific implementations of the system.

Suitable Device

FIG. 1 is a block diagram illustrating an overview of a representative device on which the system operates to recommend wellness program tasks to a user. Device 100 can be a personal computer, server, laptop, smartphone (e.g., an iPhone®), wearable device, tablet device, mobile device, or other microprocessor-based system or programmable consumer electronic device. Device 100 includes a central processing unit (CPU) 110 and one or more input devices 120. The input devices 120 can include a mouse, keyboard, touchscreen, infrared sensor, touchpad, camera, medical sensor such as a heart rate monitor or blood pressure monitor, microphone, or the like. If a mobile device, the CPU 110 is also connected to sensors (not shown) that provide information about the location and orientation of the mobile device. Such sensors may include Global Positioning System (GPS) or other position detection sensors, gyroscopes or geomagnetic position sensors to determine orientation and angular velocity of the mobile device, and accelerometers to determine changes in rate of speed of the device.

The CPU 110 can be a single processing unit or multiple processing units in a device or distributed across multiple devices. The CPU 110 can be coupled to other hardware devices, for example, via a serial or parallel bus such as a small computer system interface (SCSI) bus. The CPU 110 can communicate with a hardware controller for devices, such as a display 130 that is used to display text and graphics to a user. For example, a user can view recommended wellness programs, a wellness program itinerary, and completed tasks for each wellness program. The display 130 may be integrated with or separate from the input devices 120. Examples of a display 130 are an LCD display screen, an LED display screen, or a projected display. Input/output (I/O) devices 140 can also be coupled to the CPU 110, such as an interface component (e.g., USB, FireWire, or other interface port) or other external device such as a storage device, camera, printer, speakers, flash memory, CD-ROM drive, or DVD drive.

The device 100 also includes a communication component (not shown in FIG. 1) for wireless and wire-based communication. For example, the device 100 can communicate using the Institute of Electrical and Electronics Engineers (IEEE) 802.11 Wireless Local Area Networks standard. The communication component can communicate with another device or a server through a network using, for example, TCP/IP protocols.

The CPU 110 can access memory 150. Memory 150 includes one or more hardware devices for volatile and non-volatile storage, and can include both read-only and writable memory. For example, memory 150 can comprise random access memory (RAM), CPU registers, read-only memory (ROM), and writable non-volatile memory, such as flash memory, hard drives, magnetic storage devices, and device buffers.

Memory 150 contains computer-executable instructions, such as routines executed by the CPU 110. Memory 150 can include program memory 160 that stores programs and software, such as an operating system 162, a task modulation coordinator 164 (described in more detail below), and other applications 166. Memory 150 also includes data memory 170 that is used to store such user data as passwords, usernames, input text, audio, video, user preferences, configuration data, settings, user options, and time stamps. Data in program memory 160 and data memory 170 can be read, modified, and deleted by the CPU 110.

As shown in FIG. 1, device 100 includes a task modulation coordinator 164, wellness program coordinator 172, task engine 174, environment engine 176, user state engine 178, and task scheduler 180 modules. These modules contain instructions that, when executed by the system, implement the methods or functions of the system described herein. The modules can include or call subcomponents or other logical entities that assist with or enable the performance of some or all of these methods or functions. These modules can communicate with each other, meaning that they share data and analysis results between modules. The operation of each module will be described briefly, followed by a more detailed explanation of the overall system operation with respect to FIGS. 2-8B.

As an overview, the wellness program coordinator 172 provides a recommended set of wellness programs to a user. In particular, the wellness program coordinator 172 receives information about a user (e.g., age, height, weight, and medical conditions), determines a population segment that corresponds to the user (e.g., a 50- to 60-year-old healthy individual who is not getting enough sleep), determines a keyword or keywords associated with the population segment (e.g., sleep deprivation, dehydrated, stressed), and searches a database of wellness programs with the determined keyword or keywords.

In response to the database search, the wellness program coordinator 172 receives results that identify a set of wellness programs. The wellness program coordinator 172 filters the resulting set of wellness programs based on sponsor data (e.g., an employer, healthcare provider, or insurance company can have sponsor criteria that relate to enrollment requirements for wellness programs, such as a sponsor goal), historical success rates (e.g., based on the user having successfully completed similar wellness programs in the past), and user preferences. Based on searching and filtering, the wellness program coordinator 172 presents a curated set of recommended wellness programs to a user and receives user selections of wellness programs. The set of wellness programs selected by the user will be referred to herein as an "itinerary." By accessing the itinerary, a user is able to obtain information about each wellness program in the itinerary and the tasks associated with each wellness program. The wellness program coordinator 172 monitors and updates the itinerary of wellness programs, for example, when the user adds a wellness program or completes a wellness program. More details regarding the wellness program coordinator 172 are described in U.S. patent application Ser. No. 15/097,108, filed Apr. 12, 2016, titled "WELLNESS PROGRAM CURATION," all of which is hereby incorporated by reference in its entirety.

Using wellness program itinerary information maintained by the wellness program coordinator 172, a task engine 174 retrieves task data and metadata associated with each wellness program in the itinerary. As new wellness programs are added to an itinerary, the number of tasks associated with the itinerary grows. Conversely, as wellness programs are completed, the number of tasks associated with the itinerary shrinks.

In addition to retrieving task data and metadata, the task engine 174 monitors the completion of wellness program tasks. In some embodiments, the task engine 174 determines if a task is complete based on querying a user. For example, the task engine 174 can ask a user, "Did you complete the running task for your fitness wellness program?" Alternatively, or in addition to querying a user, the task engine 174 can retrieve information from a user's computing device that can be used to assess whether tasks have been completed.

For example, the task engine 174 can retrieve data from a user's FITBIT® wearable monitor to confirm that a user has walked 10,000 steps in a day.

The environment engine 176 retrieves and monitors data related to the user's environment. The environment of the user encompasses the physical location of the user and the immediate surroundings of the user, weather conditions at the physical location, and other factors associated with the location. The environment engine 176 retrieves environment data by determining a user's location. The environment engine 176 can estimate a user's location using a variety of technologies, such as by retrieving Positioning System (GPS) coordinates from the user's mobile device or wearable device, using services that estimate the location of a user based on the user's IP address or WiFi hotspot that the user is accessing, triangulation of the location the user's mobile device based on cell tower location, or the like. In the event that the environment engine 176 is unable to determine the actual location of the user, the environment engine may use a ZIP code of the user's home address that is obtained during a registration process of the user as a default location of the user.

Based on a user's physical location, the environment engine 176 retrieves information associated with the user's environment. The environment engine 176 can access third-party services (e.g., a weather service) to determine the current weather and forecast for a user's environment. The environment engine 176 can also determine the proximity of a user to a business (e.g., gym), public area (e.g., park, public pool, ocean, or trailhead), or other location by accessing a third-party mapping service. For example, the environment engine can determine how close the user is to a park, lake, or public swimming pool based on the distance between the user's location and the corresponding landmark.

The user state engine 178 retrieves and monitors information related to a user's state. A user's "state" includes information about the user's physical or mental health. The system uses information about the user's physical or mental health to determine whether the user is able to perform certain tasks. For example, a user may have a sore ankle or a sore knee which would preclude the user from walking or running long distances. As another example, a user may be allergic to pollen during the spring and therefore unable to perform tasks that would require the user to go outside. The user state engine 178 can determine a user's state by querying the user (e.g., "Are you healthy enough to run?" or "Are you feeling physically well today?"). Alternatively, the user state engine 178 can access a user's medical records as described in U.S. patent application Ser. No. 15/097,108 to directly identify health issues that would hinder the performance of certain tasks.

Based on information gathered from the wellness program coordinator 172, the task engine 174, the environment engine 176, and the user state engine 178, a task scheduler 180 determines a set of recommended tasks to provide to a user for the next task period. The task scheduler 180 compiles a set of tasks associated with all wellness programs in a user's current wellness program itinerary. Based on the user's environment, the user's state, and the number of remaining tasks in an itinerary that should be completed within a certain time period set for each wellness program, the task scheduler 180 determines a recommended set of tasks to provide to a user for the next task period. In identifying the recommended set of tasks, the task scheduler 180 can prioritize those tasks associated with wellness programs that have less time remaining to complete over other tasks associated with wellness programs having more time remaining to complete. In other words, the task scheduler may priorities tasks from a wellness program that is to be completed in one week over tasks associated with a wellness program having four weeks left to complete. If all tasks have the same amount of time remaining, the task scheduler 180 can use random selection to select a task.

As an example, the task scheduler 180 can receive data indicating that the user is enrolled in an itinerary with 10 wellness programs, each having a 10-week recommended time period to complete, and each with 5 tasks, for a total of 50 tasks to complete in 10 weeks. Also, the task scheduler 180 can receive data and metadata associated with each task such as physical activities required by the task (e.g., ability to run), weather restrictions (e.g., not raining to perform task), and preferred location (e.g., close to gym). Based on the received information form the other modules, the task scheduler 180 recommends a set of tasks for the next task period from the total tasks remaining for the user to complete. The task period is the period of time that the system schedules in advance for the user. Although typically one day in length, the task period length may be configured by the user or by the system operator. For example, a task period can alternatively be 2 hours, 2 days, 1 week, etc. When recommending tasks to the user, the task scheduler 180 adjusts the recommended tasks to a user to account for new wellness programs that have been added to the user's itinerary or to remove wellness programs when a user completes all tasks in a wellness program.

Suitable Environment

Figure 2:
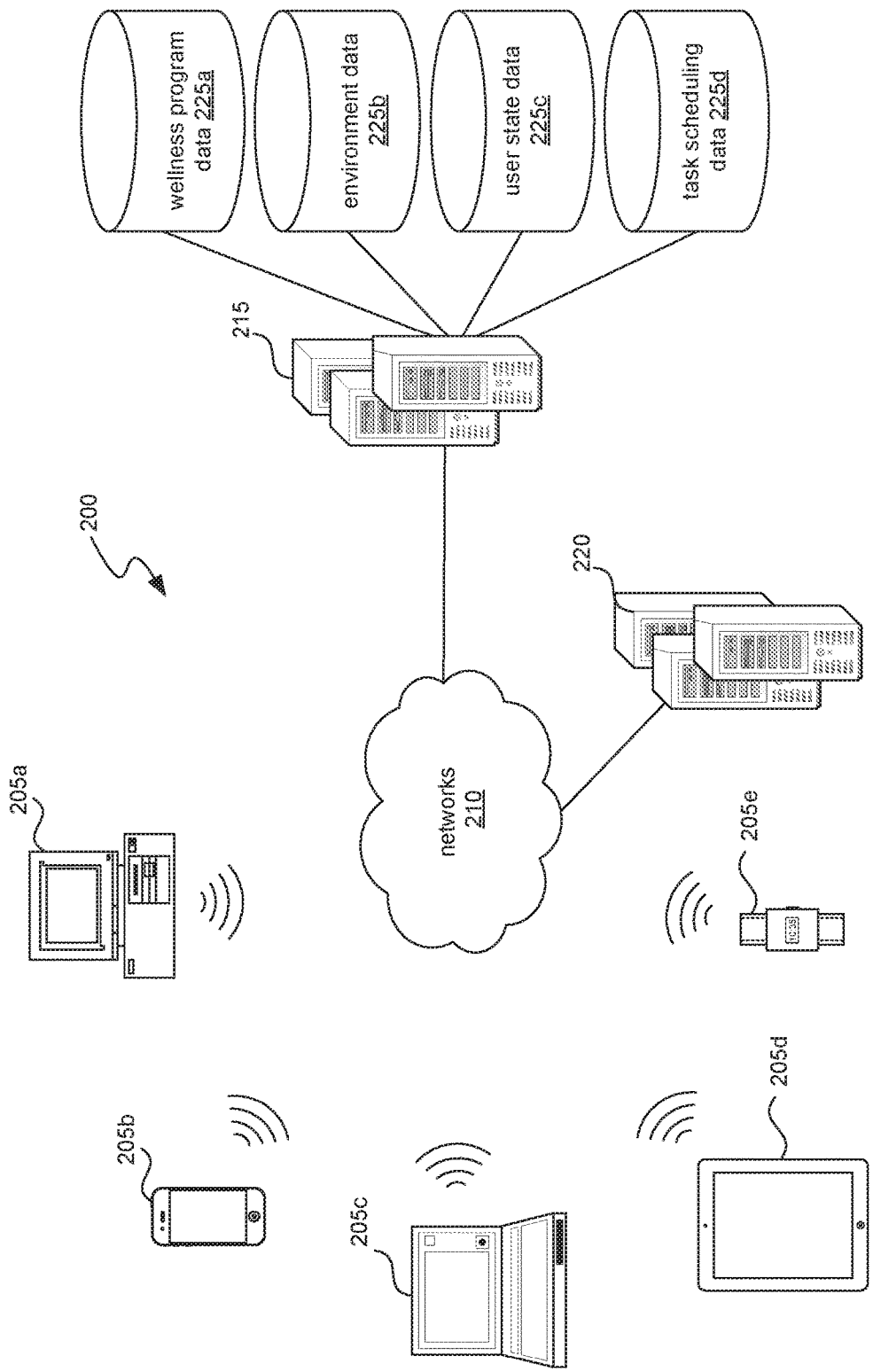
FIG. 2 is a block diagram illustrating a representative environment in which the disclosed system operates.

FIG. 2 is a block diagram illustrating a representative environment 200 in which implementations of the disclosed system can operate. The environment 200 includes one or more computing devices 205a-205e. Computing devices 205a-205e can be a desktop computer 205a, a mobile phone 205b, a laptop computer 205c, a tablet 205d, or a wearable device 205e, such as a smartwatch, etc. Computing devices 205a-205e communicate over networks 210 to system servers 215. The system servers 215 can be single servers or may be part of a distributed computing environment encompassing multiple servers located at the same or at geographically disparate physical locations. Those skilled in the relevant art will further recognize that certain portions of the system may reside on one or more system servers 215, while other portions reside on the computing devices 205a-205e. System servers 215 may communicate with one or more third-party services, represented by servers 220.

The networks 210 allow for communication in environment 200. The networks 210 may include wireless networks such as, but not limited to, one or more of a Local Area Network (LAN), Wireless Local Area Network (WLAN), Wide Area Network (WAN), Global System for Mobile Communications (GSM), Bluetooth, WiFi, Fixed Wireless Data, and 2G, 2.5G, 3G, 4G, 5G, and LTE networks, using messaging protocols such as TCP/IP, SMS, MMS, or any other wireless data networks or messaging protocols. The networks 210 may also include wired networks.

To facilitate providing a recommended subset of tasks to a user, the system accesses one or more datasets, including a wellness program dataset 225a, an environment dataset 225b, a user state dataset 225c, and a task scheduling dataset 225d. System modules can store information in these datasets or update information in these datasets continuously, periodically, or sporadically.

The wellness program dataset 225a contains data and metadata related to each wellness program in an itinerary. For each of the wellness programs in the itinerary, the dataset includes, but is not limited to, a description of the wellness program, a description of the one or more tasks associated with the wellness program, and an expected length of time to complete each wellness program. For example, a wellness program designed to improve user health may include tasks to perform physical exercise, watch a short video, answer a short quiz, stretch once a day, etc. In such an example, the wellness program may have a recommended length of 5 weeks to complete all tasks.

As an example of wellness program data, FIG. 3A depicts a representative wellness program table 300 that includes information about each wellness program. Each row in the table reflects a wellness program. Each column in the table contains data characterizing the wellness program. Some stored characteristics of wellness programs can include the wellness program name, a brief description of the program, a length of the program, keywords characterizing the wellness program, and a list of tasks associated with the program. While table 300 represents wellness programs in a table format, the wellness data may be stored in a different format (e.g., in a tree structure). Moreover, the table may include links to data stored elsewhere. For example, as shown by the underlining in table 300, some words are links or pointers to more information, such as detailed information about a particular task. The details about each task may include instructions and other content that is provided by the wellness program to the user to characterize the task. Also, while not shown in FIG. 3A, wellness program table 300 can store information that indicates a wellness program is similar to another wellness program. In some implementations, wellness programs are similar if the keywords characterizing the wellness programs are the same or differ by a limited number of words. In some implementations, the table contains links or pointers to other similar wellness programs.

Returning to FIG. 2, also included in the wellness program dataset 225a is task information for each task associated with a wellness program. Task information generally includes a task number, a short task description, an estimated task length, a characterization of any physical activities associated with the task, any weather restrictions associated with the task, and any location restrictions associated with the task. In general, when making recommendations, the system utilizes the task descriptions to determine which tasks should be included or excluded from any recommendation.

FIG. 3B depicts a representative task table 350 that includes information regarding tasks in a wellness program. Each row in the table reflects a task within a wellness program. Each column in the table contains data characterizing the task. Table 350 includes columns containing a task number, a short description of the task, the estimated length of time that it takes to complete the task, any physical activities associated with the task, any weather restrictions that might impact performance of the task, and any location restrictions or preferences for completing the task, if one exists. While table 350 represents tasks in a table format, the task data and metadata may be stored in a different format (e.g., in a tree structure). Moreover, the table may include links to data stored elsewhere. As shown by the underlining in table 350, some words are links or pointers to more information, such as detailed information about a particular task.

FIG. 3C depicts a table 370 that is used by the system to compare physical activities necessary to complete a task with health conditions that could prevent the user from performing the task. Each row in the table 370 reflects a different physical activity and the corresponding one or more health conditions that could prevent or hinder a user from performing the corresponding activity. For example, row 380 reflects the physical activity of "run," and can be associated with any wellness program task that has a component requiring the user to run. Column 275 includes a non-exhaustive list of potential health conditions that could prevent the user from running, such as leg pain, influenza, broken or sprained ankles, and/or a knee injury. As will be described in additional detail herein, if the system determines that a user has one or more of the corresponding health conditions associated with a task's activity, the system omits the task from the recommendations made to the user. It will be appreciated that the table 370 is depicted in simplified form solely for explanatory purposes. In actual implementations, the table can be linked to medical conditions defined using International Classification of Diseases codes (e.g., ICD-9 or ICD-10). By maintaining a mapping of medical conditions to different physical activities, the system operator is able to quickly identify potential restrictions as new wellness tasks are created. In some embodiments, however, the system operator may maintain a table that directly correlates medical conditions with each wellness task. Although table 370 represents the physical activities in a table format, the data and metadata may be stored in a different format.

Returning to FIG. 2, the environment dataset 225b stores and maintains data and metadata regarding the environment for a user. The environment dataset 225b includes the last known physical location of the user, the weather at the physical location, and the relative location of the user to any landmarks for completing tasks. The system can create the environment dataset 225b by accessing third-party databases and the user's computing device. Third-party databases can be accessed via third-party servers 220. Some examples of data retrievable from third-party databases are weather conditions and map location.

The user state dataset 225c stores information about the state of the user, such as data characterizing the physical ability or mental state of the user. The system can create and maintain the user state dataset 225c by querying a user to determine if the user is in adequate physical or mental shape to complete a task. For example, the system can ask a user via a graphical interface on a mobile phone if the user has any health conditions (e.g., injuries or other limitations) that would prevent them from performing a task. Alternatively, or in addition to querying a user, the system can retrieve information from a third party via server 220 operatively coupled to a third-party database (not shown in FIG. 2). The system can access medical records for a user to determine if the user is injured (e.g., accessing ICD-9 or ICD-10 databases and other user medical records). With a user's permission, for example, the system can access and obtain the user's current medical records. In many cases, user medical records are maintained by healthcare providers and are accessible only via requests made to those providers. In some cases, the system operator may have relationships with healthcare providers that allow for the direct transfer of medical records if approved by the user. In some cases, the system can ask the user to provide login information (e.g., a username and password) to allow the system to directly access the user's medical records. If the user grants permission, the system can access available medical information (e.g., the user's blood pressure, weight, and record of chronic health conditions).

The task scheduling dataset 225d stores data and metadata regarding task scheduling information. The task scheduling dataset 225d generally includes a record of the tasks that the system has recommended that the user perform during the next task period, as well as any data associated with the completion of tasks that is collected by the system. As will be described in additional detail herein, the system periodically updates the set of recommended tasks that are presented to the user based on the user environment, state, pace of task completion, and other factors.

Flow Diagram Illustrating Example Process

Figure 4:
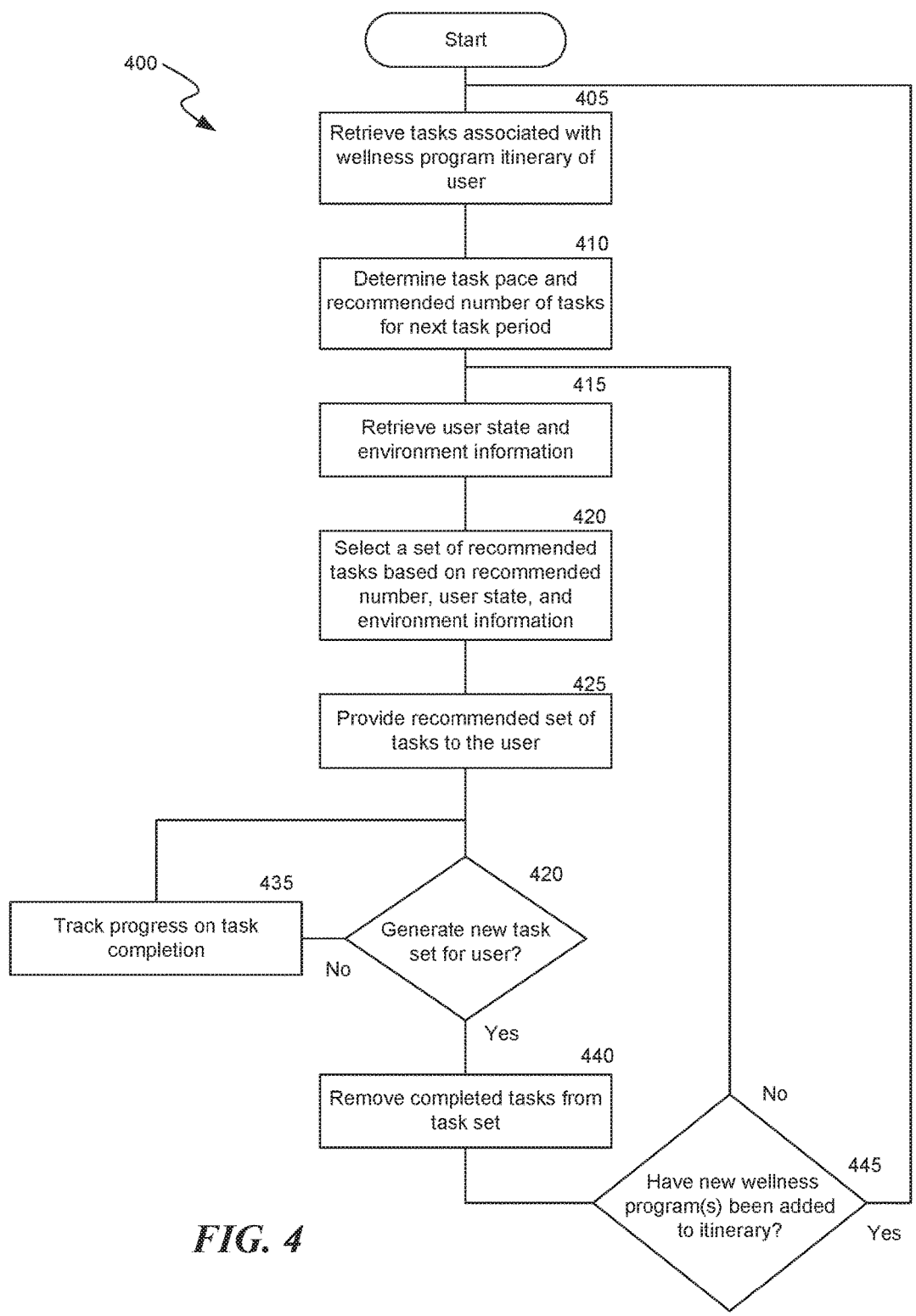
FIG. 4 is a flow diagram illustrating a process for providing a modulated set of tasks to a user.

FIG. 4 is a flow diagram illustrating a process 400 implemented by the system for generating a set of recommended tasks for a user. In general, process 400 includes retrieving tasks associated with a wellness program itinerary of the user, determining a recommended number of tasks to be completed in the next task period, retrieving user state and environment information, selecting a set of tasks based on the number of tasks, user state, and environment information, and providing the selected set of tasks to the user. The recommended tasks provided to the user change over time based on task completion progress, addition of wellness programs, and elapsed task periods. In some implementations, process 400 can be implemented on a user's computing device 205a-205e (as shown in FIG. 2), wherein the user's computing device 205a-205e communicates with a server 220 through the networks 210. Alternatively in some implementations, process 400 can be implemented solely on a computing device 205a-205e.

Figure 5A:
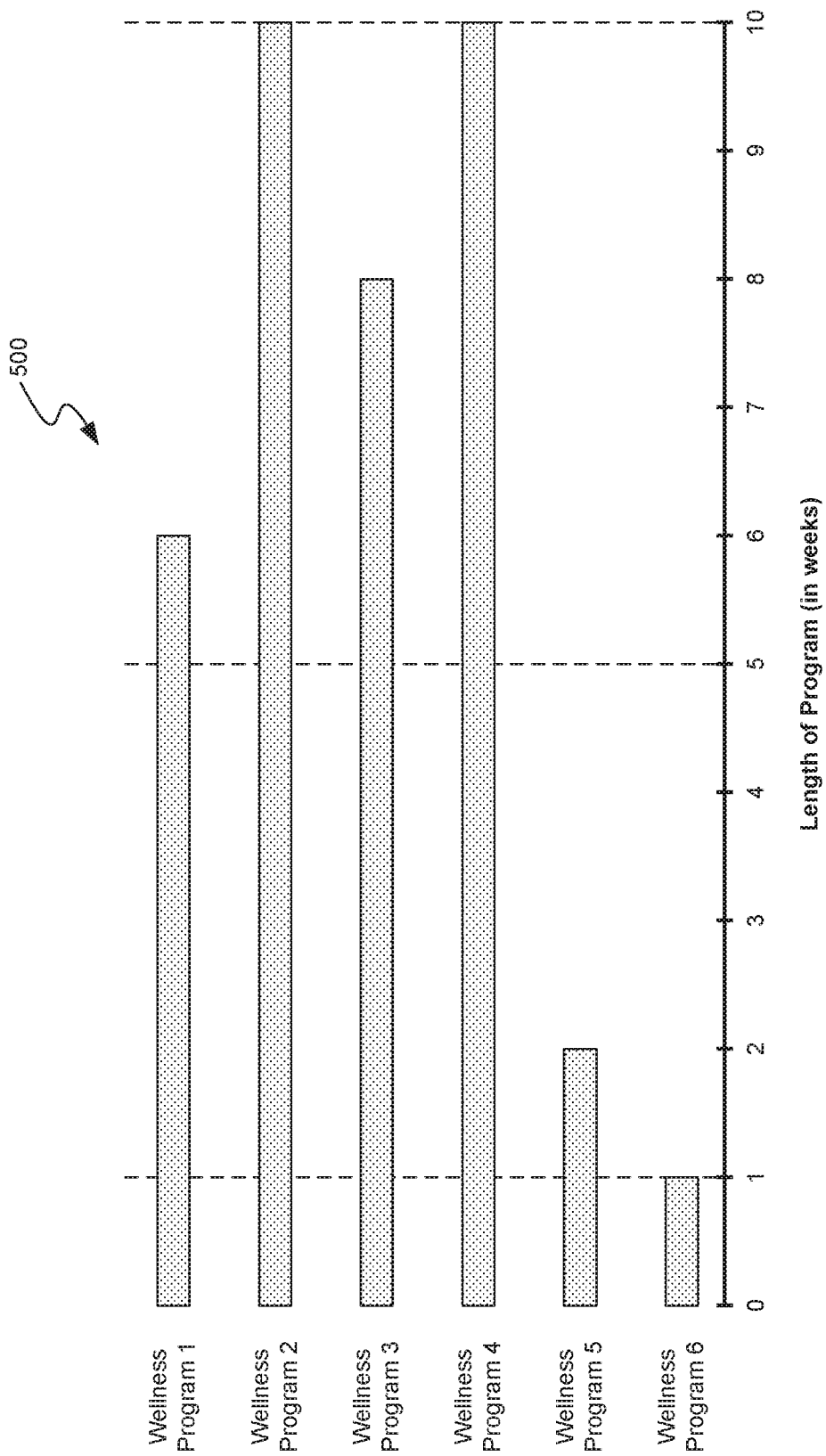
FIGS. 5A-5C include a bar graph and tables with representative wellness program itinerary data and task data of a user.

At block 405, the system retrieves information about each wellness program in the user's wellness program itinerary. The retrieved wellness program information includes the recommended length of each wellness program and the tasks associated with each wellness program. FIG. 5A is a bar chart 500 that depicts representative wellness programs contained in the itinerary of a user. As depicted in FIG. 5A, the user has six wellness programs in his/her itinerary. The y-axis of the bar chart 500 lists each wellness programs, and the x-axis represents the length of each wellness program in weeks. The shortest wellness program (Wellness Program 6) is expected to be completed within one week. In contrast, the longest wellness programs (Wellness Programs 2 and 4) are expected to be completed within 10 weeks. Although the length of wellness programs is shown in weeks in bar chart 500, the length of wellness programs can be represented in hours, days, months, etc. The bar chart 500 in FIG. 5A may depict the wellness programs lengths as initially selected by the user, or may depict the remaining program lengths after the user has been completing tasks within the wellness programs for a period of time.

Returning to FIG. 4, at block 405 the system also retrieves information characterizing each task of the wellness programs in the user's itinerary. Information characterizing each task may include a short description of the task, activities required to complete the task, physical requirements to perform the task and correlated health conditions as previously described in FIG. 3C, weather conditions that could impact performance of the task, location restrictions associated with the task, and other information, such as is previously described with respect to FIG. 3B. For example, the system could retrieve tasks and associated task information for a user who has an itinerary with wellness programs to lose weight and improve focus at work. The tasks associated with the itinerary can include tasks for exercising at a gym, walking in a park, and watching videos.

At block 410, the system determines the number of tasks to recommend to the user in the next task period. A task period is a period of time for which the system projects user activities. A task period can be set by an administrator of the system or by the user. A task period typically ranges between 1-2 days, but can span periods as short as an hour or as long as one or more weeks. The number of tasks to be recommended for completion in the next task period is based on the required pace necessary for the user to complete all wellness programs within the recommended timeframe. In general, the system determines the required task pace for all wellness programs in an itinerary using the Equation 1 below:

$$\text{task pace} = \sum_{i=1}^{n}\left(\frac{\text{number of tasks remaining for wellness program }(i)}{\text{total time remaining to complete wellness program }(i)}\right) \quad (1)$$

The calculated task pace is based on the retrieved number of tasks for each wellness program and the total time remaining to complete each wellness program. The task pace is expressed in the same unit of time as used to measure the total time remaining to complete the wellness program, such as tasks/week or tasks/day. The task pace, however, is typically reflected as the number of tasks per day.

Figure 5B:
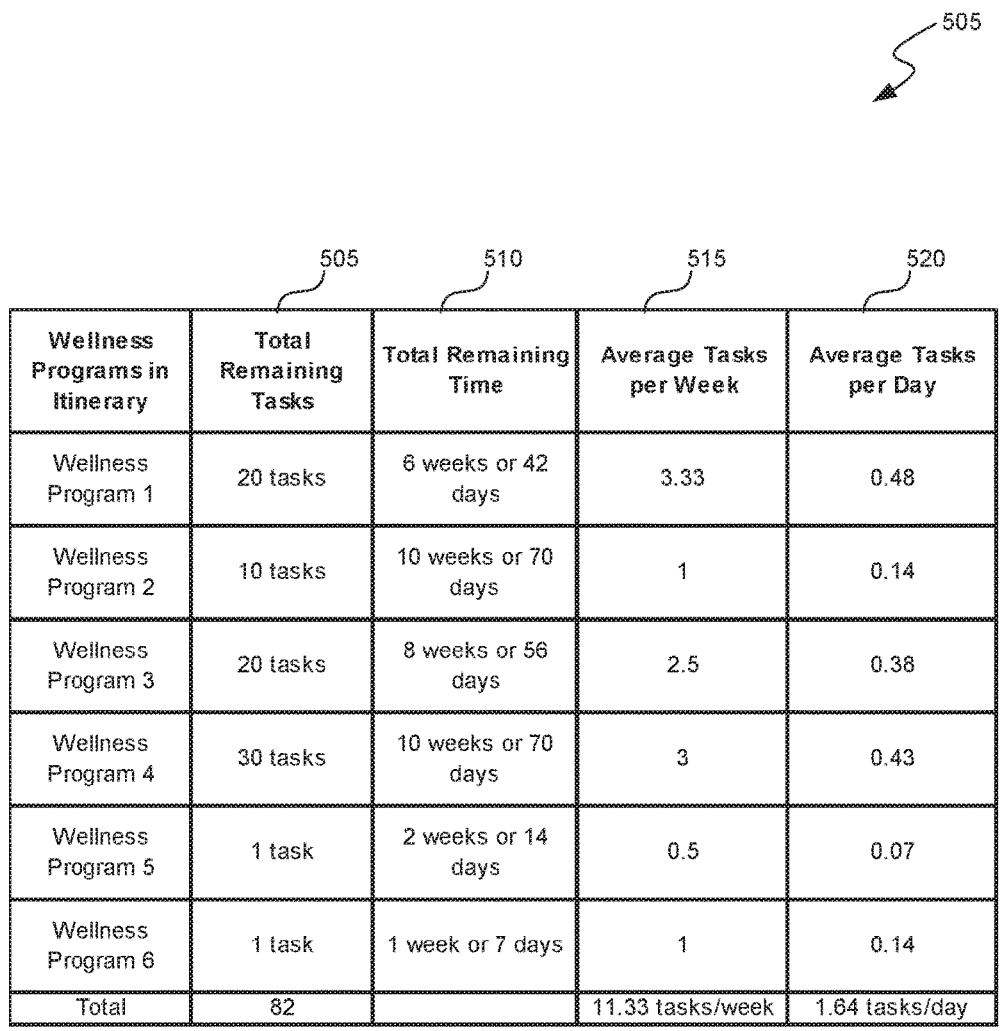

FIG. 5B depicts a table 505 that is used to demonstrate the application of Equation 1 and the calculation of the task pace. Each row in the table reflects a wellness program (e.g., Wellness Program 1) in the user's itinerary, except for the bottom row. The bottom row reflects a total (e.g., summation) of each column. Each column in the table contains data characterizing the wellness program. For example, column 510 includes data characterizing a total remaining number of tasks in the corresponding wellness program (e.g., 20 tasks for Wellness Program 1, 10 tasks for Wellness Program 2). Column 515 includes a total time remaining to complete the wellness program (e.g., 6 weeks or 42 days for Wellness Program 1, 10 weeks or 70 days for Wellness Program 2). When a wellness program is initially added to an itinerary, the total remaining tasks and the total remaining time are equal to the number of tasks in the wellness program and the expected time period to complete the wellness program (also referred to as the length of the wellness program). As time progresses and the user completes tasks, the system adjusts the totals in these columns to reflect the remaining tasks and time in each wellness program.

Using the data in columns 505 and 510, the system calculates an average number of tasks to complete per week as reflected in column 515 and an average number of tasks to complete per day as reflected in column 520 for each wellness program. The system adjusts the values in these two columns depending on the number of tasks that remain for a user to complete and the time remaining in each wellness program. For example, for Wellness Program 1 in table 500, there are 20 tasks to complete in 6 weeks. The system therefore determines that the user must complete 3.33 tasks per week or 0.48 tasks per day in order to complete the wellness program in the recommended time period. The task pace can be updated by the system as updated task completion data is received. Once the task pace for each wellness program is calculated, the system sums the pace for each wellness program in order to identify an overall task pace that must be maintained in order to complete all wellness programs in a user's itinerary within a recommended time.

In general, the first time the system determines the task pace for a user it is based on the initial conditions of a wellness program itinerary (e.g., the time period recommended for completing a wellness program and the total number of tasks in each wellness program). After a task period has expired or the user has added a wellness program to the itinerary, the system updates the task pace. Depending on the user's progress in completing tasks during the task period, the task pace may increase, decrease, or stay the same. For example, the task pace will decrease if a user has completed more tasks than necessary to complete the wellness programs in the time remaining to complete the wellness programs. Alternatively, the task pace will increase if a user has completed less tasks than necessary to complete the wellness programs in the itinerary in the recommended time period.

Returning to FIG. 4, the calculated task pace is used to determine a recommended number of tasks for the user to perform in the next task period. The recommended number of tasks is computed by scaling the task pace to reflect the length of the next task period. If the task period is one day, for example, the number of tasks to recommend is set by the system to be equal to the daily task pace. If the task period is two days, however, the system multiplies the daily task pace by a factor of two to calculate the number to tasks to recommend.

At block 415, the system retrieves user state and user environment information. The system can retrieve user state information by querying the user on a computing device. For example, the system can ask a user at the beginning of a task period, "Are you able to do physical activity today?" The user may respond by answering yes or no with his or her computing device. Also, the system can retrieve user state information by querying one or more third-party databases. For example, a user may have broken his or her leg or may have some other health condition that prevents the user from performing tasks. In such an example, with permission from the user, the system can access a user's medical records and search for ICD codes (e.g., ICD-9 or ICD-10) that indicate the existence of health conditions that would impact the ability of the user to successfully perform wellness program tasks in the user's itinerary.

In addition to retrieving user state information at block 415, the system retrieves user environment information. The system can retrieve user environment information by accessing or retrieving location information from a user's mobile computing device. The location information may include the GPS location of the mobile device, a location based on cell tower triangulation, a location based on proximity to known Wi-Fi hotspots, or any other location determination technology. If the system is unable to retrieve current location information from the user's mobile computing device, the system may use as a default location the user's home address or other location information provided by the user during a registration process with the wellness program provider.

Using the physical location of the user, the system assesses the characteristics of the user's environment. Such characteristics can include the weather (e.g., raining, sunny, cold, temperature, etc.) at the location of the user. The weather may be obtained by the system from weather services which provide location-based forecasts via API calls, such as NOAA, AccuWeather, etc. The characteristics can also include the user's proximity to landmarks (e.g., parks, beaches, bike paths) or businesses (e.g., gyms) which might help or hinder the performance of certain tasks. The proximity to landmarks is determined by the system using mapping services available via API calls, such as Google maps, MapQuest, OpenStreetMap, etc. The system can also retrieve such information from the user state dataset 225b and the environment dataset 225c described in FIG. 2.

At block 420, the system selects a set of recommended tasks for the user based on the recommended number of tasks for the next task period, user state information, and user environment information. To select tasks to provide to a user, the system filters the total set of remaining tasks in the user's wellness program itinerary to select a subset of tasks. Starting with all remaining tasks, the system executes a filtering routine to determine whether the current user state data rules out any tasks because of physical activities associated with the tasks. The system can compare a user's medical records to the physical requirements associated with each task. If the system determines that a user has a health condition that prohibits certain physical activity, the system will not recommend that the user complete a task requiring that type of activity. For example, if the state data reflects that a user is not physically able to run during the next task period, the system will not select a task that involves running. Such a filtration is performed by comparing the state information of the user with the physical requirement information contained in table 350 and table 370.

The system also executes a filtering routine to determine whether the current user environment data rules out or rules in any tasks because of location or weather. The system assesses location by determining proximity of the user to sites or landmarks that are necessary for the performance of a certain task. For example, as shown in table 350, task 5 has a location restriction of a "gym within 10 miles." Using this location restriction, the system can search for a gym within 10 miles of the user based on the GPS coordinates of the user's mobile device or other location information derived from the computing device of the user. If the system determines that a gym is within 10 miles, the system will promote the task; if the system determines that a gym is not within 10 miles, the system can remove or demote the task. As another example, task 6 in table 350 has a location restriction of a "park within 5 miles." The system can determine a user's GPS coordinates from the user's mobile device and then determine if a user is within 5 miles of a park by querying a third-party mapping service via an application programming interface (e.g., Google® Maps API, Bing Maps API, OpenStreetMap API). The system can then promote or remove task 6 based on the response to the query from the third-party mapping service.

The system assesses weather by determining the location of the user and accessing a third-party weather service via an application programming interface (e.g., AccuWeather API, Forecast.io API, NOAA API) to predict the weather around the user during the next task period. As an example, if the environment data reflects that a user is at a location experiencing a snow storm, the system will remove tasks that are based outdoors and instead promote tasks that are based indoors. Such a filtration is performed by comparing the environment information of the user with the preferred location information contained in table 350.

Once the system has filtered the remaining tasks using the state and environmental information, the system determines whether the number of filtered tasks exceeds the recommended number of tasks to present to the user during the next task period. If the number of filtered tasks is less than the recommended number of tasks, the filtered tasks may be recommended to the user. If the number of filtered tasks is greater than the recommended number of tasks, however, the system can use a random selection algorithm to select the tasks to recommend to the user. For example, if the system determines that 15 tasks are suitable for a user based on the state and environment data, but the system can recommend only 3 tasks, the system executes a random selection algorithm to choose 3 tasks from the remaining 15 tasks.

Additionally, the system can further filter tasks based on time remaining to complete a task. To accomplish this, the system can execute a prioritization algorithm at block 420. A prioritization algorithm assesses the time remaining in each wellness program, from least time remaining in a wellness program to most time remaining in a wellness program. The system uses the ranked time remaining in each wellness program to select the recommended set of tasks for a user. In general, tasks associated with wellness programs with less time remaining will be recommended in a subsequent task period before tasks with more time remaining. For example, tasks associated with a wellness program with one week remaining will be recommended in the next task period before tasks associated with wellness programs with two or more weeks remaining. Additionally, the system may not implement the prioritization algorithm if the system determines that too few tasks are available to select from. For example, if the system determines that a user has a task pace of 3 tasks per task period and 3 tasks are available to select, the system will not prioritize task recommendations.

At block 425, the system provides the recommended set of tasks to the user. Once the set of recommended tasks is provided to the user, the user can begin completing tasks. In general, the number of tasks in the recommended set of tasks provided to the user is less than the number of uncompleted tasks. For example, the user may have 50 remaining tasks associated with a wellness program itinerary, but the system may provide a list of only three tasks to the user to complete in a given task period after the aforementioned analysis.

At decision block 430, the system determines whether a new set of recommended tasks needs to be presented to the user. The determination that a new set of recommended tasks needs to be generated is based on a triggering event. A triggering event can be the start of a new task period, the completion by a user of all recommended tasks with a task period, or the addition of a new wellness program to the user's itinerary. If the system determines that a triggering event has not occurred at decision block 430, processing continues to block 435 where the system tracks the user's progress on task completion. The system can monitor the activities of a user to determine whether the user has completed a task during the task period. Monitoring can occur in at least three different ways. The system may receive an indication that a task has been completed by querying a user about certain tasks and receiving the user's response to the queries (e.g., "Have you completed a task? If so, please select the task you completed."). Alternatively, the system may monitor sensor information from mobile or wearable devices associated with a user to assess, for example, the activities of the user. For example, the system can access a user's wearable device to determine that the user has walked 10,000 steps in order to complete one of the wellness tasks. The system can monitor other information by communicating with a user's wearable device. For example, depending on the capabilities of the wearable device, the system can upload information about the heart rate of the user. Other information, such as number of steps, length of sleep, blood pressure, sweat composition, and respiratory rate of the user may also be uploaded to the system from the user's wearable device. Finally, the system may receive indications from the wellness program provider that the user has completed certain tasks, such as watching a video or taking an online quiz.

If, at decision block 430, the system detects the occurrence of a triggering event, processing continues to block 440. At block 440, the system removes all completed tasks from the set of tasks in the wellness program itinerary. At block 440, the system may query the user to confirm that certain tasks have been completed as part of the removal process.

At decision block 445, the system determines if a new wellness program or programs have been added to the user's itinerary. If a user has not added a new wellness program or programs, the system returns to block 415, where it again retrieves user state and environment information in order to begin the process of recommending a set of tasks to the user. Depending on changes to the user state and environment, the system will recommend a next set of tasks for the user to perform during the next task period. For example, after a task period ends, the weather in a user's environment may have changed from sunny to rainy, and the system provides an updated set of recommended tasks to the user based on the weather change. In such an example, the system can execute a matching or filtering algorithm to determine tasks that are suitable for a user based on user environment and associated task weather restrictions. As another example, the user may no longer be injured and now is able to complete tasks that involve physical exercise. In such an example, the system can provide running tasks in the updated task set.

Figure 5C:
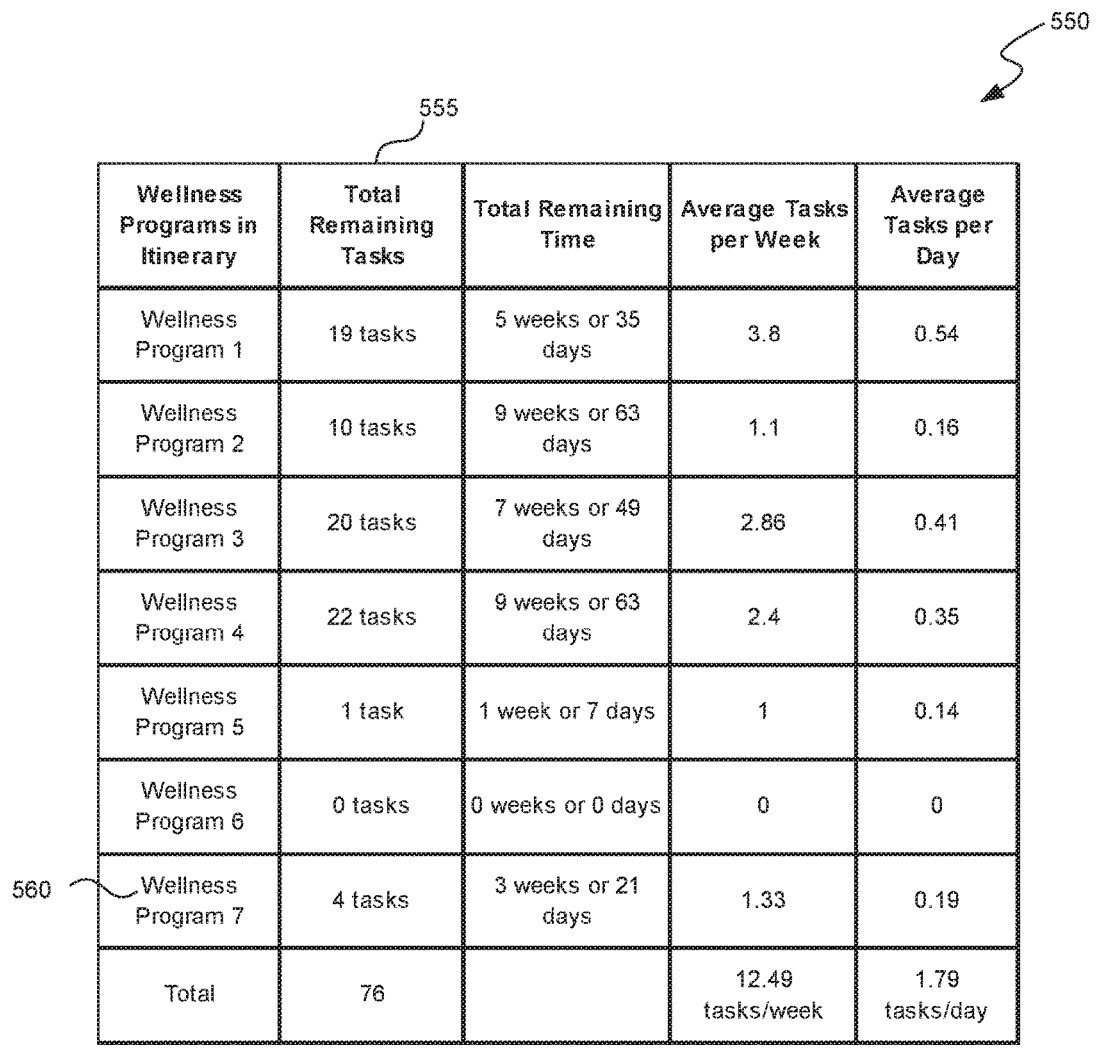
Figure 6:
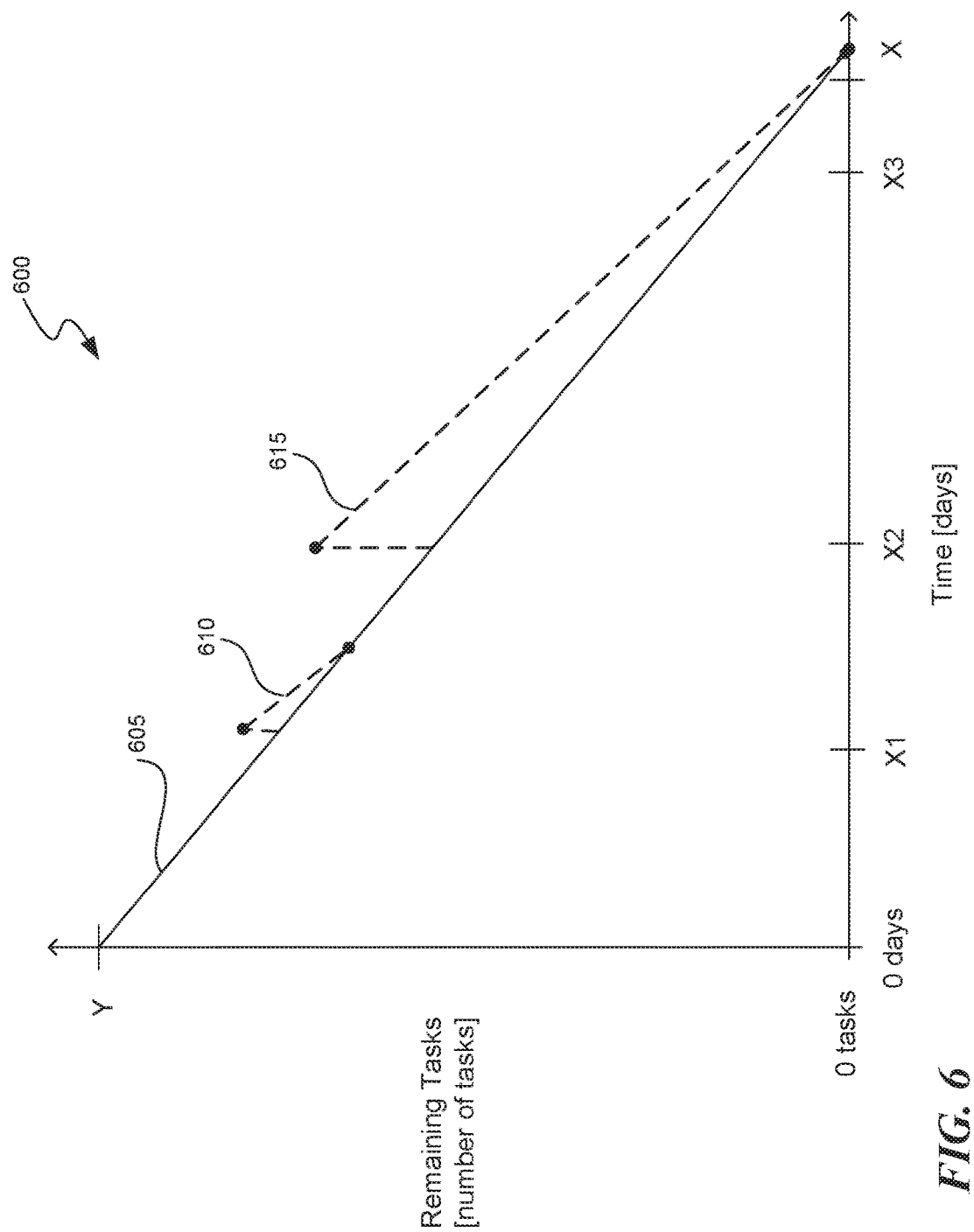
FIG. 6 is a graph depicting changes in the number of tasks that need to be performed by a user over time.

If the system determines that a new wellness program has been added to the itinerary at decision block 445, processing continues to block 405, where the process is repeated to include the additional wellness program. FIG. 5C depicts a table 550 that is based on the initial wellness program itinerary reflected in table 500, but after an elapsed period of one week. Two changes have been made to the data contained in table 500. First, certain tasks have been completed by the user during the intervening week. As a result, the system has updated the data in the task remaining column 555 to reflect the remaining tasks associated with each wellness program. Second, the user has added a wellness program 560 ("Wellness Program 7") to the itinerary. By virtue of the completed tasks and the additional wellness program, the system has re-computed the task pace necessary to complete all wellness programs in the itinerary within the recommended timeframe. While the user previously needed to complete 11.3 tasks per week in accordance with the itinerary reflected by table 500, the user now needs to complete 12.49 tasks per week in accordance with the itinerary reflected by table 550. In general, the system is constantly modifying the recommended set of tasks based on updated user environment information, user state information, task completion, and the addition of new wellness programs.

Although not shown in FIG. 4, if the system determines that all tasks have been completed and no wellness programs have been added, the process 400 can end and the system can notify the user that all tasks have been completed. Also, process 400 is repeated by the system for each user analyzed by the system and also repeated for each user as the user progresses through task periods or modifies an itinerary.

The flow diagram in FIG. 4 illustrates a representative process implemented by the system to generate a set of recommended tasks to provide to a user. Each block in the flow diagram may represent a module, segment, or portion of code that comprises one or more executable instructions for implementing the specified logical function(s). It should be noted that, in some alternative implementations, the functions noted in the blocks may occur out of the order noted in FIG. 4. For example, two blocks shown in succession may, in fact, be executed substantially concurrently, or the blocks may sometimes be executed in the reverse order, depending on the functionality involved. It should also be noted that each block of the flow diagram in FIG. 4, and combinations of blocks in the flow diagram, can be implemented by special-purpose hardware-based systems that perform the specified functions or by combinations of special-purpose hardware and computer instructions. Additionally, in some alternative implementations, some functions may be omitted or skipped. For example, the system can execute the process 400 based solely on a user environment or based solely on a user state. Also, although not shown in FIG. 4, prior to retrieving tasks associated with a wellness program itinerary, the system may have generated a curated set of wellness programs, and the user may have selected to enroll in a few of the curated wellness programs (generating and providing a curated set of wellness programs is further described in U.S. patent application Ser. No. 15/097,108).

To further illustrate the process 400 described above, FIG. 6 is a graph that depicts the number of remaining tasks in a hypothetical user's wellness program itinerary over time. Graph 600 illustrates changes to the user's task pace based on completion of tasks by the user and the addition of wellness programs to the itinerary. The x-axis of graph 600 reflects units of time (days) and the y-axis reflects number of remaining tasks. The task pace is therefore represented by the slope of line 605 in graph 600. At day zero, when the user starts the wellness program itinerary, the user has Y tasks to complete. Based on the number of wellness programs selected by the user, the user is projected to complete all tasks in the itinerary by time X.

One adjustment to the task pace is represented by an event at time X1, in which a user completed fewer tasks than the recommended number of tasks for the prior task period. The user may have completed fewer tasks because the system determined that no suitable tasks were available to recommend to the user during the task period (e.g., the system determined that rainy weather and the physical requirements of the task resulted in no suitable tasks for the task period). Alternatively, a user may have forgotten to complete a task during a task period. As a result of completing fewer tasks than recommended in a task period, the task pace of the user is increased in order to put the user back on track to complete all tasks within the recommended timeframe (i.e., the slope of line 610 is steeper than the slope of line 605).

Another adjustment to the task pace is represented by an event at time X2, which is the addition of a wellness program to the user's itinerary. The additional wellness program has new tasks, causing the remaining number of tasks to increase. The addition of new tasks also increases the task pace, as represented by the slope of line 615 being steeper than line 605.

Figure 7A:
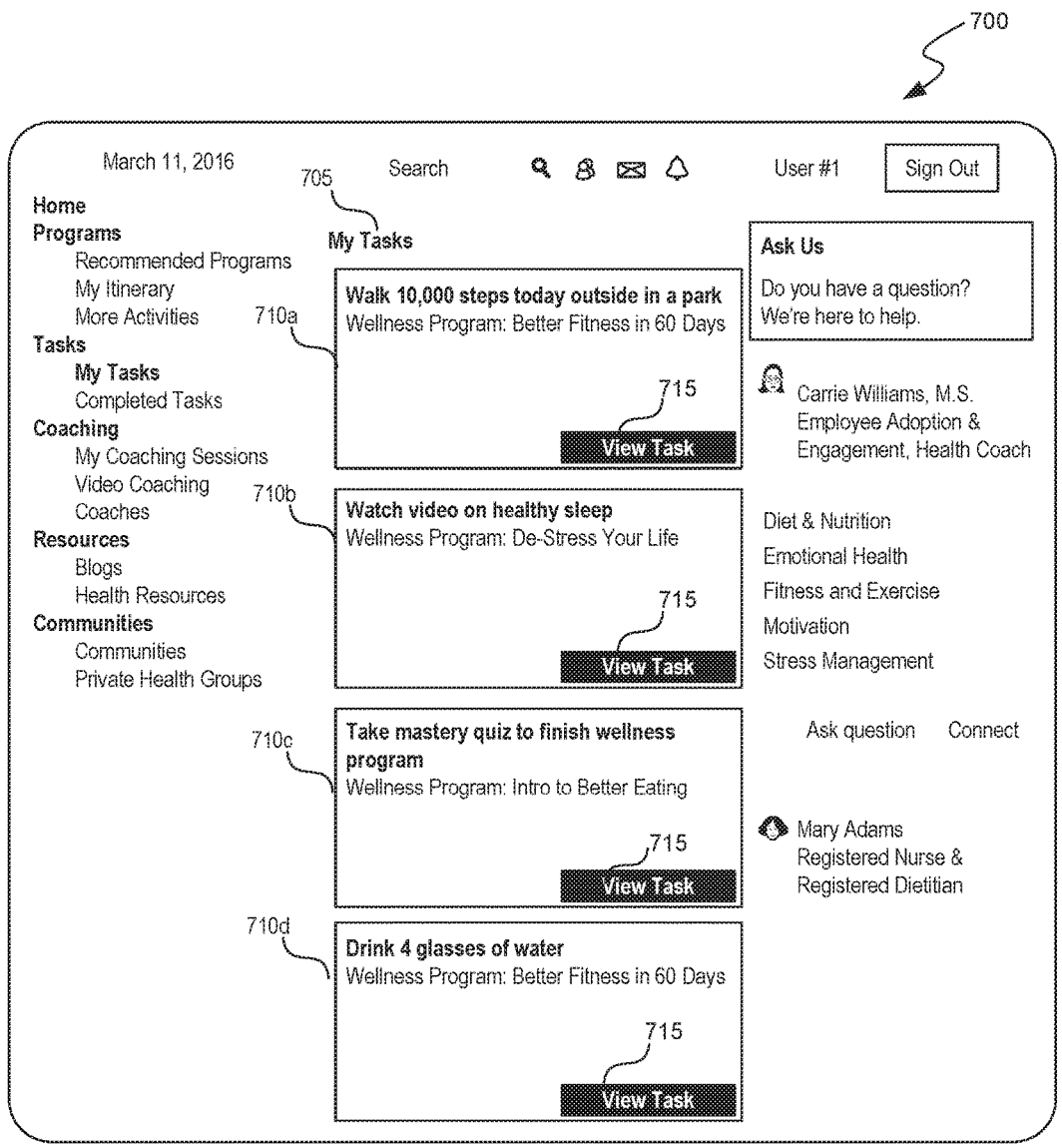

Once the system presents the recommended set of tasks to the user, the user can view the recommended set of tasks on a graphical interface. FIG. 7A is a graphical user interface 700 that is generated by the system, from which the user can view information about wellness programs, the itinerary for the wellness programs, and other related information. As shown, the left side of graphical interface 700 has interactive buttons or widgets that a user can select to view particular information, such as wellness programs in which the user is currently enrolled, or coaching sessions the user has viewed or should view to complete a task for a wellness program. Also, the left side of graphical interface 700 includes resources the user can access, such as blogs and other health resources (e.g., articles or websites). The right side of graphical interface 700 includes other interactive buttons and widgets for the user.

The center of the display includes a "My Tasks" region 705. The My Tasks region 705 depicts four recommended tasks associated with the itinerary that the user is enrolled in.

The system generated the set of four tasks based on the process 400 described above. The four recommended tasks 710a-710d presented to the user in graphical interface 700 are walk 10,000 steps outside in a park (associated with a "Better Fitness in 60 days" wellness program), watch a video on healthy sleep (associated with a "De-Stress Your Life" wellness program), take a mastery quiz (associated with an "Intro to Eating Better" wellness program), and drink four glasses of water (also associated with the "Better Fitness in 60 days" wellness program). The user can view more information about a task by pressing a "View Task" button 715. In response to pressing the "View Task" button 715, the system can display information about the task such as a description, duration, and activity required to complete the task for the selected wellness program. As shown in FIG. 7A, graphical user interface 700 has tasks that are likely performed in good weather (e.g., the tasks have weather restrictions requiring sunny conditions).

Even though the system could display many or all of the tasks a user needs to complete for each wellness program in the graphical interface 700, the system displays a subset of tasks based on the necessary task pace, the environment of the user, the state of the user, and the progress on completed tasks for the user. By controlling the number of tasks displayed to a user, the user is not overwhelmed with too many tasks. Also, by providing tasks that are suitable for the user based on environment and user state information, the system is likely to encourage a user to complete tasks that he or she will enjoy.

Figure 7B:
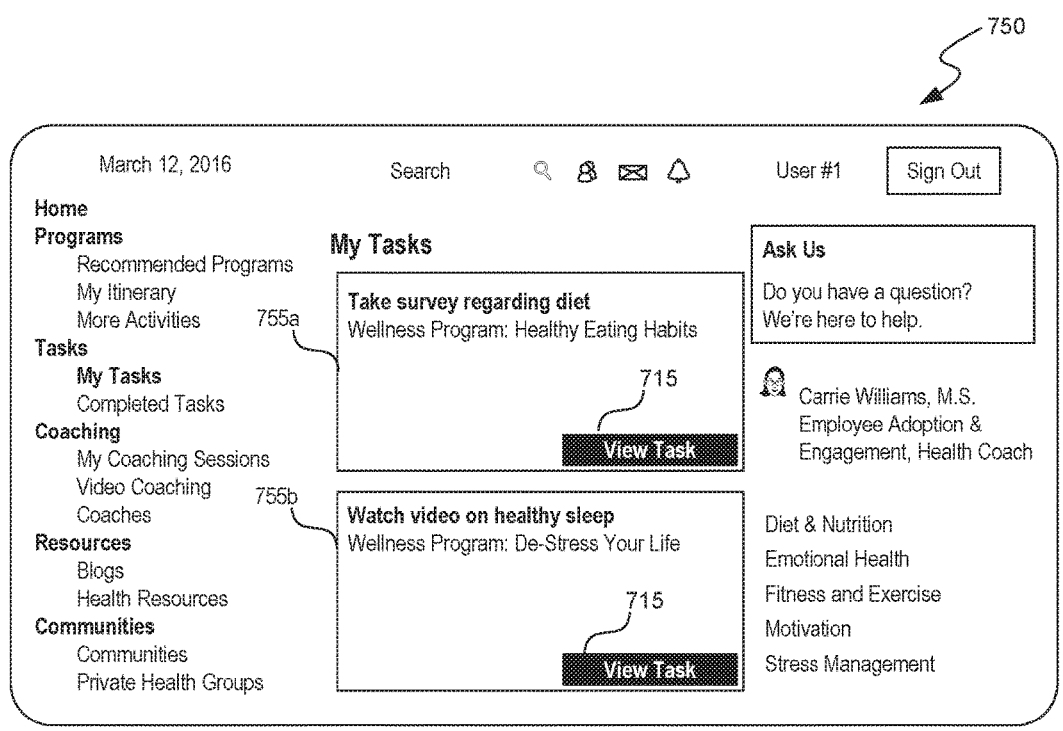

FIG. 7B includes a graphical interface 750 that is generated by the system for a new task period. The graphical interface 750 provides a recommended task set with two tasks and not four tasks, based on completion of prior tasks and changes in task pace, state, or environmental conditions. The two tasks are to take a survey regarding diet associated with the "Healthy Eating Habits" wellness program (task 755a), and to watch a video on healthy sleep (task 755b). The system may have provided these two tasks for a variety of reasons, as described above. One reason may be that a new task period has started (e.g., the day has ended), or that the weather is different compared to the previous task period. Alternatively, the user may have completed a task and the task has been removed from the task set, or the user may have failed to complete a task, and the ask is therefore carried over into the next task period.

Figure 8A:
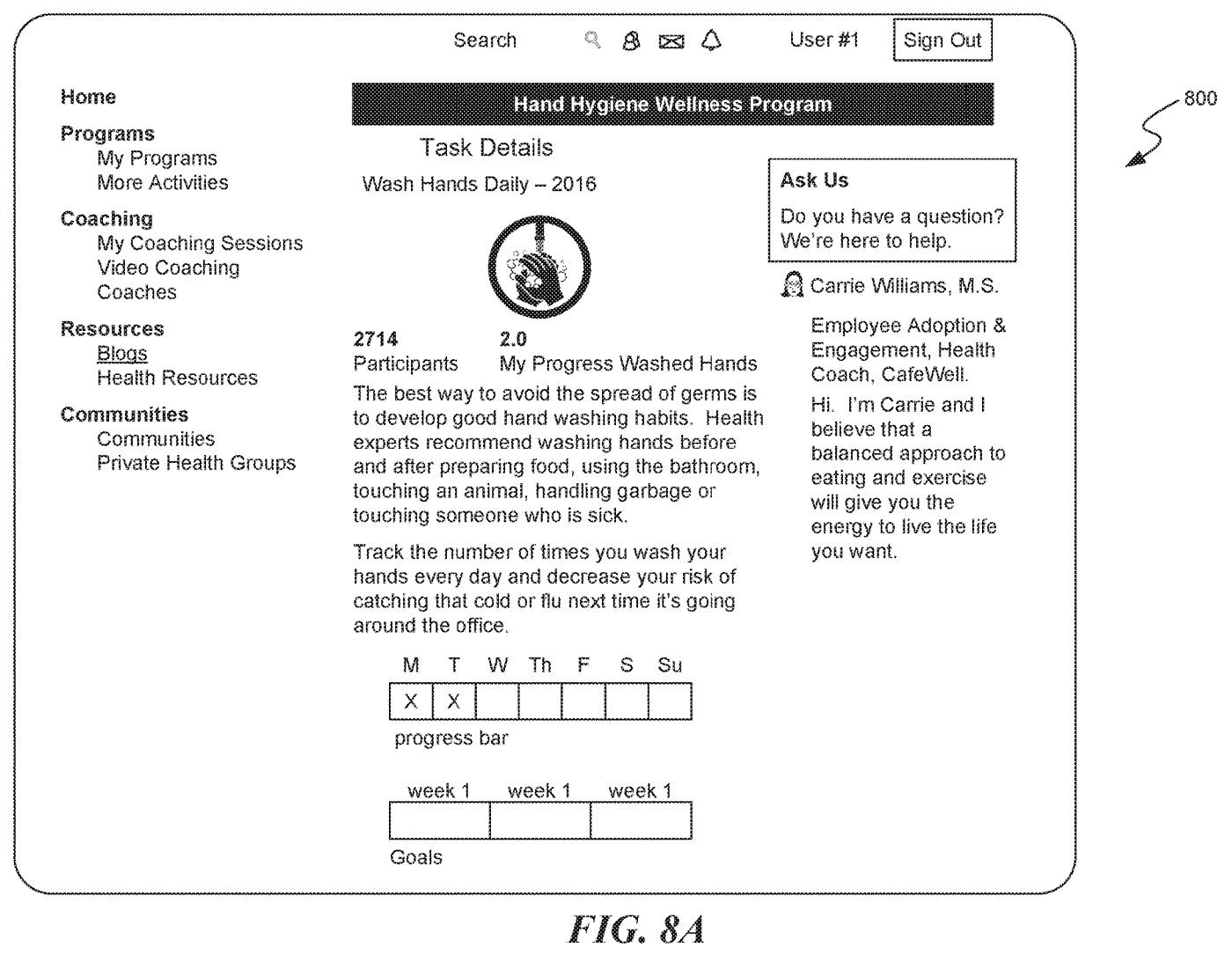

Along with providing a graphical interface to view a modulated task set, the system allows the user to record and view his or her progress on each task. FIG. 8A is a graphical user interface 800 that is generated by the system for viewing task progress for a wellness program. In the graphical interface 800, the user is shown his or her task progress related to the "Hand Hygiene" Wellness Program. For example, the user can see that he or she successfully completed the task of washing his or her hands on Monday and Tuesday, but he or she still needs to wash his or her hands for the rest of the week to complete the goal. In general, the system can provide task activity details for each wellness program, or the itinerary of wellness programs in which a user is enrolled.

In addition to providing task progress information, the system can provide a graphical interface for recording task progress. FIG. 8B is a graphical user interface 850 that is generated by the system for recording task progress related to the "Healthy Habits" Wellness Program. In the graphical interface 850, the user is shown information related to a task of drinking water. The user may use a "Log Now" button 855 to record that he or she completed the task of drinking one glass of water. In general, the system can provide logging or recording options for each task associated with a wellness program. Alternatively, the system may automatically determine a user has completed a task based on sensor information in a user's device (e.g., a FITBIT® or pedometer).

From the foregoing, it will be appreciated that specific implementations of the invention have been described herein for purposes of illustration, but that various modifications may be made without deviating from the scope of the technology. Accordingly, the technology is not limited except as by the appended claims.

We claim:

1. A method implemented by a computing system to modulate a set of tasks associated with a plurality of wellness programs, the method comprising:
for each wellness program in a plurality of wellness programs associated with a user:
retrieving a time remaining to complete the wellness program;
retrieving tasks remaining to complete the wellness program;
determining a recommended number of tasks to be completed in a next task period based on the time remaining to complete each wellness program and a total number of tasks remaining for each the wellness program;
retrieving state data associated with the health of the user based on obtaining sensor data from a sensor;
retrieving environment data based on a location of the user based on determining the location of a mobile device associated with the user;
selecting a set of recommended tasks for the user to complete in the next task period, the recommended tasks selected from the tasks remaining to complete for each wellness program, the selection based on the recommended number of tasks to be completed in the next task period, the user state data, and the user environment data;
providing the selected set of recommended tasks to the user; and
generating a revised set of recommended tasks for the user based on updated user state data, updated user environment data, and task completion progress for the user.

2. The method of claim 1, wherein generating the revised set of recommended tasks comprises:
tracking the task completion progress by the user; and
after a triggering event:
retrieving the updated user state data and the updated user environment data,
determining a second recommended number of tasks to be completed based on the time remaining to complete each wellness program and a total number of tasks remaining for each the wellness program; and
generating a modified recommended set of tasks for the user based on the updated user state data, the updated user environment data, and the second recommended number of tasks.

3. The method of claim 2, wherein the first triggering event is a task period elapsing, a request to add a new wellness program to the wellness program itinerary, or an indication that all tasks in the recommended set of tasks have been completed.

4. The method of claim 1, wherein the user environment data is further based on retrieved weather conditions associated with the location of the user.

5. The method of claim 1, wherein retrieving user environment data comprises retrieving information on surrounding landmarks based on the location of the user.

6. The method of claim 2, wherein tracking progress of task completion for the user comprises querying the user to determine whether a task has been completed or receiving data from a mobile device associated with the user that reflects that the task has been completed.

7. The method of claim 1, wherein the state data associated with the health of the user is further based on medical records received from a health provider service.

8. The method of claim 1,
wherein the user state data includes data that indicates a task has a physical requirement, and
wherein selecting the set of recommended tasks comprises identifying tasks capable of being performed by the user with the physical requirement.

9. The method of claim 1, wherein the determined location of the mobile device associated with the user is based on determined Global Positioning System (GPS) coordinates.

10. The method of claim 1, wherein the next task period is a single day, two days, or a week.

11. A non-transitory computer-readable storage medium containing instructions that, when executed by one or more processors, perform to modulate a number of tasks provided to a user, the method comprising:
for each wellness program in a plurality of wellness programs associated with a user:
retrieving a time remaining to complete the wellness program;
retrieving tasks remaining to complete the wellness program;
determining a recommended number of tasks to be completed in a next task period based on the time remaining to complete each wellness program and a total number of tasks remaining for each the wellness program;
retrieving state data associated with the health of the user based on obtaining sensor data from a sensor;
retrieving environment data based on a location of the user based on determining the location of a mobile device associated with the user;
selecting a set of recommended tasks for the user to complete in the next task period, the recommended tasks selected from the tasks remaining to complete for each wellness program, the selection based on the recommended number of tasks to be completed in the next task period, the user state data, and the user environment data;
providing the selected set of recommended tasks to the user; and
generating a revised set of recommended tasks for the user based on updated user state data, updated user environment data, and task completion progress for the user.

12. The non-transitory computer-readable storage medium of claim 11, wherein generating the revised set of recommended tasks comprises:
tracking task completion progress by the user; and
after a triggering event:
retrieving the updated user state data and the updated user environment data,
determining a second recommended number of tasks to be completed based on the time remaining to complete each wellness program and a total number of tasks remaining for each the wellness program; and
generating a modified recommended set of tasks for the user based on the updated user state data, the updated user environment data, and the second recommended number of tasks.

13. The non-transitory computer-readable storage medium of claim 12, wherein the first triggering event is a task period elapsing, a request to add a new wellness program to the wellness program itinerary, or an indication that all tasks in the recommended set of tasks have been completed.

14. The non-transitory computer-readable storage medium of claim 11, wherein the user environment data is further based on retrieved weather conditions associated with the location of the user.

15. The non-transitory computer-readable storage medium of claim 11, wherein retrieving user environment data comprises retrieving information on surrounding landmarks based on the location of the user.

16. The non-transitory computer-readable storage medium of claim 12, wherein tracking progress of task completion for the user comprises querying the user to determine whether a task has been completed or receiving data from a mobile device associated with the user that reflects that the task has been completed.

17. The non-transitory computer-readable storage medium of claim 11, wherein the state data associated with the health of the user is further based on medical records received from a health provider service.

18. The non-transitory computer-readable storage medium of claim 11,
wherein the user state data includes data that indicates a user has a physical requirement, and
wherein selecting the set of recommended tasks comprises identifying tasks capable of being performed by the user with the physical requirement.

19. The non-transitory computer-readable storage medium of claim 11, wherein the determined location of the mobile device associated with the user is based on determined Global Positioning System (GPS) coordinates.

20. The non-transitory computer-readable storage medium of claim 11, wherein the next task period is a single day, two days, or a week.

* * * * *